United States Patent
Baker et al.

(10) Patent No.: US 7,279,152 B2
(45) Date of Patent: Oct. 9, 2007

(54) USE OF POLYPHOSPHATE AS A TOOTH EROSION INHIBITORS IN ACIDIC COMPOSITIONS

(75) Inventors: Nicola Jane Baker, Little Fransham (GB); David Myatt Parker, Hereford (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

(21) Appl. No.: 10/240,047

(22) PCT Filed: Mar. 23, 2001

(86) PCT No.: PCT/EP01/03280

§ 371 (c)(1),
(2), (4) Date: Feb. 13, 2003

(87) PCT Pub. No.: WO01/72144

PCT Pub. Date: Oct. 4, 2001

(65) Prior Publication Data

US 2004/0091517 A1    May 13, 2004

(30) Foreign Application Priority Data

Mar. 27, 2000 (GB) ................................. 0007421.1

(51) Int. Cl.
*A61K 8/46* (2006.01)
*A61Q 11/00* (2006.01)
(52) U.S. Cl. ........................ 424/57; 426/548; 426/590; 433/215; 433/217.1
(58) Field of Classification Search ................ 426/590, 426/599; 424/57, 601, 602, 603, 606; 433/215, 433/216; 514/102, 901
See application file for complete search history.

(56) References Cited

U.S. PATENT DOCUMENTS

| 3,968,263 A | 7/1976 | Reussner |
| 4,080,440 A | 3/1978 | DiGiulio et al. |
| 5,017,362 A | 5/1991 | Gaffar et al. ................. 424/52 |
| 5,096,701 A | 3/1992 | White et al. .................. 424/52 |
| 5,939,052 A | 8/1999 | White et al. .................. 424/52 |
| 6,022,576 A | 2/2000 | Cirigliano et al. .......... 426/597 |
| 6,126,980 A | 10/2000 | Smith et al. ............. 426/330.3 |
| 6,187,295 B1 | 2/2001 | Glandorf ..................... 424/52 |
| 6,383,473 B1 | 5/2002 | Parker |
| 6,719,963 B2 | 4/2004 | Parker |
| 6,908,909 B2 | 6/2005 | Parker |
| 6,984,376 B2 | 1/2006 | Stephenson et al. |
| 2002/0102220 A1 | 8/2002 | Stephenson ................. 424/49 |

FOREIGN PATENT DOCUMENTS

| FR | 2 731 588 | 9/1996 |
| JP | 61036211 | 2/1986 |
| JP | 04139120 | 5/1992 |
| JP | 09-295942 | 11/1997 |
| WO | WO 96/26648 | 9/1996 |
| WO | WO 98/22080 | 5/1998 |
| WO | WO 99/21432 | 5/1999 |
| WO | WO 00/13531 | 3/2000 |
| WO | WO 01/00048 A1 | 1/2001 |
| WO | WO 01/52796 A2 | 7/2001 |
| WO | WO 01/52796 A3 | 7/2001 |

OTHER PUBLICATIONS

English language translation of Japanese Patent 9-295942, Publication Date Nov. 18, 1997, pp. 1-10.*
Van Der Reijen, "Influence of Polymers for Use in Saliva Substitutes on De- and Remineralization of Enamel in vitro", Caries Res., vol. 31, pp. 216-223 (1997).*
Lussi et al., "The Influence of Different Factors on in vitro Enamel Erosion", Caries Res., vol. 27, pp. 387-393 (1993).*
Harris et al., "The Effect of Phosphate Structure on Dental Caries Development in Rats" *J. Dent. Res.*, vol. 46 (1), pp. 290-294 (1967).

* cited by examiner

*Primary Examiner*—Frederick Krass
(74) *Attorney, Agent, or Firm*—Dara L. Dinner; Theodore R. Furman; Charles M. Kinzig

(57) ABSTRACT

The use of polyphosphate in acidic oral compositions, especially acid beverages with a pH between 2.2 and 5.5, to alleviate or prevent the tooth damage associated with the consumption of acid. The invention may be practiced using polyphosphate alone or in combination with calcium and/or viscosity modifying polymers.

34 Claims, No Drawings

USE OF POLYPHOSPHATE AS A TOOTH EROSION INHIBITORS IN ACIDIC COMPOSITIONS

This application is the §371 National stage entry of PCT/EP01/03280, filed 23 Mar. 2001.

The present invention relates to the use of polyphosphate in acidic compositions for oral use such as foodstuffs, in particular acidic beverages, and oral healthcare compositions, to alleviate or prevent the tooth damage associated with consumption of acid, namely dental erosion.

Dental erosion describes the "pathologic, chronic, localised, painless loss of dental hard tissue chemically etched away from the tooth surface by acid and/or chelation without bacterial involvement" (Imfeld, 1996, Eur J. Oral Sci. 104, 151-155.). The acids causing the erosion are derived from dietary, occupational or intrinsic sources and are not products of the intraoral flora. Therefore dental erosion is a condition distinct from and different to dental caries with dis-similar etiology. With the trend towards an increase in eating and drinking frequency amongst all age groups it is likely that the incidence of dental erosion will increase. When a product such as a beverage is prepared in accordance with this invention, and introduced into the oral cavity for consumption or healthcare purposes, the dissolution or removal of calcium and phosphate from teeth by chemical processes is significantly reduced.

Lussi et al (1995, Caries Res 29, 349-354) have associated the pH and titratable acidity of a beverage with its erosive potential; the greater the concentration of acid in the beverage the more damaging to teeth it became. Similarly a study in children (Millward et al, (1994) Int. J Paed. Dent. 4, 151-157.) associated the presence of dental erosion with the consumption of acidic beverages and fruit juices.

EP 551398 discloses a method for preventing the erosion of tooth enamel by consuming an acid beverage (having a pH of less than 5.5) comprising from 0.02% to 0.15% of calcium in the form of a calcium citrate malate complex having a molar ratio of citrate to malate of 1:0.5 to 1:4.5.

WO 97/30601 discloses acid-based liquid compositions having reduced tooth erosion properties containing a calcium compound and an acidulant in which calcium is present in the range of 0.3 to 0.80 mol per mol of acidulant and the pH of the composition is from 3.5 to 4.5.

WO 00/13531 discloses the use of viscosity modifying polymer materials, commonly used as thickening agents, stabilisers and emulsifiers, in acidic compositions for oral use to alleviate or inhibit the tooth damage associated with the consumption of acid.

The present invention is based on the discovery that effective reduction of tooth erosion in acidic oral compositions can be achieved by the addition of polyphosphate. For the purposes of this invention, polyphosphate is defined as a polymer of phosphate where the number of phosphate groups in the polymer (n) is at least 3 or preferably at least 4. Best practice of the invention is achieved when n is equal to or greater than 4, suitably equal to or greater than 7 and preferably equal to or greater than 12. Compositions where the average chain length (n) is from about 12 to 28 have been found to be particularly effective, for example 12, 17, 20, 21, 25 and 28.

Furthermore, it has surprisingly been found that the inhibitory effect on dental erosion due to acid is enhanced by addition of polyphosphate together with calcium or with a viscosity modulating polymer as described in WO 00/13531. Such combinations of polyphosphate and calcium or polyphosphate and a viscosity modifying polymer in an acidic composition for oral use have been found to reduce the loss of calcium and phosphate from tooth enamel to a greater extent than is conferred by addition of either calcium or viscosity modifying polymer alone. Acidic compositions for oral use which are palatable, storage stable and effective in reducing dental erosion due to acid may accordingly be formulated with less calcium per mole of acid and at lower pH values than are disclosed in WO 97/30601.

Accordingly, the present invention provides the use of polyphosphate as a tooth erosion inhibitor in an acidic composition for oral administration.

Polyphosphates for use in the present invention will be pharmaceutically acceptable and preferably food grade materials suitable for use in foodstuffs. A preferred polyphosphate is sodium polyphosphate. Concentrations of sodium polyphosphate for best practice of the invention are from 0.005 g/l to over 2 g/l, suitably from 0.01 g/l to 1.5 g/l, and preferably from 0.01 g/l to 1 g/l. Whilst benefit from use of polyphosphate has been observed at concentrations up to and including 3 g/l, the inclusion of larger quantities of polyphosphate has been found to reduce the benefit, indicating that the concentration of polyphosphate employed is an important aspect of the invention. Polyphosphoric acid applied at an equivalent molar concentration to sodium polyphosphate may also be used, as may other salts of polyphosphoric acid, such as potassium salts, provided they have suitable solubility in acidic applications. Appropriate adjustments to quantities may be required dependent upon the nature of the polyphosphate counterion present.

The invention is applicable to all acidic products for oral consumption or use. These include acidic beverages, vinegars, sauces, pickles, preserves, confectionery, frozen comestibles such as ice lollies and diverse acidic products such as acidic dairy products, and also to other substances, suitably in liquid or semi-solid form, to be taken orally such as acidic oral healthcare products, for example mouth washes, and medicines.

The invention is particularly suitable for application to a variety of solid, semi-solid or liquid foodstuffs, especially acidic beverages. These include still and carbonated alcoholic and non-alcoholic beverages, for example fruit drinks, ciders and wines and in particular health drinks such as blackcurrant juice drinks or vitamin added beverages.

The invention also extends to concentrates and powdered forms for preparing acidic beverages, eg. by dilution or dissolution in water. In a preferred embodiment, the acid composition is a ready to drink beverage or a drink concentrate for dilution prepared from a natural fruit juice such as blackcurrant juice.

The invention is advantageously applied to acidic compositions, in particular foodstuffs and especially beverages, containing natural and/or added acidulants. The acid composition may contain organic and/or inorganic acids and may be supplemented with vitamins such as ascorbic acid. Preferred acidulants include potable acids such as citric, malic, lactic, phosphoric, acetic and tartaric acids and mixtures thereof. The invention is advantageously applied to drink products containing natural or added citric acid.

The acidulant concentration in a composition according to the invention will be determined by the type of product, the desired effective pH, the desired organoleptic properties and the acidity of the chosen acid source. The acidity of a composition may be expressed in terms of titratable acidity which is a measure of the percentage weight of acid present in a solution as calculated from the volume of sodium hydroxide required to neutralise the acidic species present. In practice, titratable acidity is measured potentiometrically with standardised sodium hydroxide solution of a known concentration at a temperature of 20 degrees Centigrade. A typical beverage will have a titratable acidity in the range 0.01 to 4% w/w and a typical fruit-based ready to drink beverage will have a titratable acidity in the range 0.1 to 2% w/w. Typically the acid concentration in compositions of the invention, for example the acid concentration in a fruit-based product would be in the range 0.01% w/w to 4% w/w, suitably in the range 0.1% w/w to 2.5% w/w. A typical ready to drink fruit beverage based on citric and/or malic acid as the acidulant will have an acid concentration in the range 0.01 to as great as 2% w/w, preferably 0.01 to 1.0% w/w of the beverage composition. In a concentrate for dilution, typical citric/malic acid concentration will be in the range 0.1 to 4% w/w of the composition. Mixtures of potable acids may be used, for example mixtures of acids selected from citric, malic, phosphoric and lactic acids and other suitable food grade excipients known in the art Foodstuffs such as beverages may be unsweetened or sweetened with natural sugars or synthetic sweeteners such as saccharine, aspartyl phenyl alanyl methyl ester, or other sweeteners known in the art. Compositions may also contain other conventional additives such as sodium benzoate, sorbic acid, sodium metabisulfite, ascorbic acid, flavourings, colourings and carbon dioxide.

Practice of the invention does not give rise to taste defects. Surprisingly we have found that erosive potential of acidic formulations may be minimised by the addition of polyphosphate salts to acidic preparations at low pH values and optionally low levels of calcium and/or a viscosity modifying polymer. These features endow the preparations with highly acceptable organoleptic parameters.

The effective pH of compositions for oral use according to the invention will vary according to type of product, acid content and desired organoleptic properties. Typically, use of polyphosphate according to the invention will be practised with control of pH and the effective pH will be less than or equal to 5.5 and preferably less than or equal to 4.5. A typical effective pH range of compositions is from as low as pH 2.2 to as high as pH 5.5, suitably from pH 2.4 to pH 4.5, preferably from pH 2.4 to pH 4.0, and more preferably from pH 2.7 to pH 4.0, especially for beverages containing fruit acids.

The term effective pH is used in the context of the present invention to mean the pH of the composition when in liquid form or the pH of the composition before solidification (where the composition is a solid or semi-solid prepared via a liquid phase intermediate) or the pH of a solid or semi-solid composition when reconstituted or dissolved in a liquid, eg. water. The term solidification encompasses the treatment or supplementation of liquid phase intermediates to form a solid or semi-solid.

Advantageously, use of polyphosphate according to the invention is used in combination with control of pH and/or addition of calcium and/or addition of viscosity modifying agents such as hydrocolloids.

The pH of the formulation may be adjusted to the desired range by the addition of an appropriate alkaline compound e.g. sodium hydroxide or a suitable salt for example sodium carbonate, bicarbonate, citrate, malate or lactate. Similarly, suitable potassium and calcium compounds may be employed for this purpose. Alternatively, acidulants for example citric acid, malic acid, lactic acid, phosphoric acid or food-approved mineral acids may be employed to reduce the pH if so desired.

If polyphosphate is to be used in conjunction with the addition of calcium then the concentration of calcium used will vary according to the nature and concentration of the acids and the nature and concentration of the polyphosphate present. The acid solution may contain organic and/or inorganic acids and may be supplemented with vitamins such as ascorbic acid. In a concentrated beverage, to be diluted with up to five parts of water prior to consumption, the calcium concentration may vary from 0.001 mol per litre (40 ppm) to more than 0.05 mol per litre (2000 ppm). In a ready to drink beverage the calcium ion concentration may vary from 0.0002 mol per litre (10 ppm) to more than 0.01 mol per litre (400 ppm). In a ready to use liquid form the preferred range is from 0.00125 to 0.0125 mol per litre (50 ppm to 500 ppm) calcium, more preferably from 0.00125 to 0.01 mol per litre (50 ppm to 400 ppm), yet more preferably from 0.00125 to 0.005 mol per litre (50 ppm to 200 ppm). Calcium content may also be calculated on a molar basis relative to the molarity of the acidulant. Calcium may be present in an amount up to 0.8 mol per mol of acidulant. The molar ratio of calcium to acid may be from 0.01 to 0.75, is likely to be from 0.05 to 0.6, and typically from 0.1 to 0.5 for a fruit-based beverage product.

Those skilled in the art will appreciate that the combination of calcium and polyphosphate in solution must be approached with caution to avoid the formation of insoluble hazes and precipitates that may occur at higher levels of calcium, although the presence of insoluble matter is dependent to a degree on the concentration and nature of acidulant, the concentration and nature of the polyphosphate preparation and in particular to the pH of the solution.

If added, calcium may be added as any convenient salt such as calcium carbonate, calcium hydroxide, calcium citrate, calcium malate, calcium lactate, calcium chloride, calcium phosphate, calcium glycerophosphate or calcium formate or any other salt to minimise any adverse flavour contribution to the composition.

In a particularly preferred embodiment of the invention, polyphosphate is used in combination with a viscosity modulating polymer material. Suitable viscosity modulating polymer materials for use in the invention include food grade complex polysaccharide stabilisers and thickening agents such as alginates, locust bean gum, gellan gum, guar gum, gum arabic, tragacanth, carrageenan, acacia gum, xanthan gums, pectins, cellulose derivatives such as carboxymethylcellulose and other such natural or semi-synthetic polymer materials used in the field of foodstuffs and other compositions for oral use, including mixtures of one or more thereof. A suitable synthetic, non-polysaccharide viscosity modulating polymer is polyvinylpyrrolidone (PVP).

Preferred complex polysaccharide materials for use in the invention include alginates, xanthans, cellulose derivatives and pectins. Combinations of such materials with polyphosphate are particularly effective. The addition of a complex polysaccharide to compositions has been shown to confer benefit with respect to inhibition of tooth erosion at very low concentrations. For example, the concentration of polysaccharide required to practice the invention may be as low as 0.005% w/v. Benefit has been demonstrated at concentrations up to 1.0% w/v and the upper concentration limit is likely to be determined by the desired viscosity of the composition. For a typical polysaccharide such as xanthan gum, the concentration required to practice the invention is suitably from 0.005 to 0.1% w/v, more preferably from 0.01 to 0.05% w/v.

Preferred pectins are in particular low and high methoxy pectins, low ester pectins and amidated or partly amidated pectins. Suitable alginates include commercially available low, medium and high viscosity alginate products. For example, low viscosity propylene glycol alginate and sodium alginate sold under the trade names Kelcoloid LVF and Manucol LF by Monsanto; medium viscosity sodium alginate sold under the trade name Manucol DH by Monsanto; and high viscosity propylene glycol alginate sold under the trade name Kelcoloid HVF by Monsanto. Suitable xanthans include a range of products available from Monsanto under the trade names Keltrol T, Keltrol RD, Keltrol TF, Keltrol SF and Keltrol BT. Suitable pectins include high methoxy pectins such as Unipectin QC40 available from SKW Biosystems; low ester pectins such as products sold under the trade names GENU LM 22 CG and GENU LM 12 CG, partly amidated low ester pectins such as products sold under the trade names GENU LM 101 AS and GENU LM 102 AS, and amidated low ester pectins such as the product sold under the trade name GENU LM 104 AS FS, all of which pectin products are available from Hercules Ltd.

Oral compositions containing polyphosphate for use according to the present invention may also contain magnesium or other ions as adjuncts for remineralisation. It may also contain an effective amount of malic acid or potable salts thereof to maintain the solubility of the calcium (when added) so as to prevent or minimise the precipitation of insoluble calcium salts. Added malic acid may provide as little as 10% of the total acidity of the beverage, the remainder of the acidity being provided by other, preferably naturally present, acids such as citric acid, or by ascorbic acid.

In a preferred embodiment, the acid composition is a drink concentrate prepared from a natural fruit juice, such as blackcurrant juice, for example a flavoured syrup concentrate. The polyphosphate may be added either to the concentrate, especially when the beverage is sold to the consumer as a concentrate for dilution before drinking, or when diluting the syrup concentrate for preparation of a "ready to drink" diluted concentrate. Optionally the product contains reduced levels of sugar or carbohydrate or is of low calorie type containing intense sweeteners.

The beverages may be prepared by mixing the ingredients according to conventional methods. The solid ingredients may be dissolved in water or in hot water if required prior to addition to the other components. Typically drinks are pasteurised prior to filling in bottles or cans or other packs or are "in-pack pasteurised" after filling.

In a further aspect, the invention provides the use of polyphosphate, suitably being a phosphate polymer wherein the number of phosphate groups (n) is at least 3, preferably at least 7 and more preferably at least 12, as a tooth erosion inhibitor, in the manufacture of an orally administrable acidic composition.

In a yet further aspect, the invention provides a method of reducing the tooth erosion potential of an orally administrable acidic composition comprising adding to the composition a polyphosphate, suitably being a phosphate polymer wherein the number of phospate groups (n) is at least 3, preferably at least 7 and more preferably at least 12.

The invention also extends to a method of reducing tooth erosion caused by acid in orally administrable acidic compositions by orally administering an acidic composition comprising a polyphosphate, suitably being a phosphate polymer wherein the number of phospate groups (n) is at least 3, preferably at least 7 and more preferably at least 12.

The following examples are illustrative of the invention.

EXAMPLE 1

Test solutions were prepared by dissolving the ingredients in water as described in the Table. For test solutions containing sodium polyphosphate, the average chain length (n) of the polyphosphate polymer used was 17. All solutions were prepared to give a pH of 3.0 and a titratable acidity of 0.5% w/v CAMH (citric acid monohydrate). Where calcium was added, the molar ratio of calcium: citric acid used was about 0.08. The erosive effect of the solutions was evaluated using in-vitro planometry tests in which flat dental enamel sections were exposed to test solutions at a temperature of 37° C. for 4 hours. The method of measurement has been described by Davis and Winter 1977, British Dental Journal 143, 116-119. Erosive effect was evaluated by physical measurement of the depth of enamel (in microns) lost during the procedure.

| Phosphate Salt | Phosphate salt (g/L) | Ca (ppm) | Xanthan Gum (% w/v) | 4 Hr Enamel Loss | SD |
|---|---|---|---|---|---|
| None | 0 | 0 | 0 | 38.9 | 8.4 |
| None | 0 | 0 | 0 | 53.7 | 2.4 |
| Na polyphosphate (n ≈ 17) | 0.5 | 0 | 0 | 18.8 | 0.7 |
| Na polyphosphate (n ≈ 17) | 3 | 0 | 0 | 24.5 | 1.9 |
| None | 0 | 80 | 0 | 41.1 | 5.7 |
| None | 0 | 80 | 0 | 80 | 10 |
| Na polyphosphate (n ≈ 17) | 0.25 | 80 | 0 | 7.4 | 1.1 |
| Na polyphosphate (n ≈ 17) | 0.5 | 80 | 0 | 5.5 | 0.7 |
| Na polyphosphate (n ≈ 17) | 0.5 | 80 | 0 | 6.9 | 1.4 |
| Na polyphosphate (n ≈ 17) | 1 | 80 | 0 | 10.9 | 0.6 |
| Na polyphosphate (n ≈ 17) | 1 | 80 | 0 | 11 | 1.3 |
| Na polyphosphate (n ≈ 17) | 3 | 80 | 0 | 33.4 | 1.1 |
| None | 0 | 0 | 0.05 | 5.6 | 0.4 |
| Na polyphosphate (n ≈ 17) | 0.5 | 0 | 0.05 | 1.2 | 0.2 |
| Sodium phosphate | 0.65 | 80 | 0 | 33.4 | 4.6 |
| Tetra-sodium pyrophosphate | 1.08 | 80 | 0 | 28.6 | 2.1 |
| Penta-sodium triphosphate | 0.61 | 80 | 0 | 20.1 | 1.8 |

Calcium, added as calcium carbonate (BDH Merck Ltd, Poole, Dorset, UK).
Citric acid monohydrate (CAMH) (BDH Merck Ltd, Poole, Dorset, UK).
Xanthan gum (Keltrol RD, Monsanto, Tadworth, Surrey, UK).
Sodium Polyphosphate 96% (Sigma-Aldrich Chemical Co, Poole, Dorset, UK).
Sodium phosphate, ACS grade (Sigma-Aldrich Chemical Co, Poole, Dorset, UK).
Tetra-sodium pyrophosphate (deca-hydrate), AnalaR grade (BDH Merck Ltd, Poole, Dorset, UK).
Penta-sodium triphosphate, (BDH Merck Ltd, Poole, Dorset, UK).
pH was adjusted to 3.0 in all cases by the addition of sodium hydroxide (BDH Merck Ltd, Poole, Dorset, UK).

Whereas a control solution, representing a typical beverage composition with respect to acid concentration and pH, comprising 0.5% citric acid, pH 3.0 resulted in a loss of at least 40 microns of enamel, a test solution to which had been added 0.5 g/l sodium polyphosphate resulted in a loss of about 20 microns of enamel demonstrating a substantial reduction in erosive effect. Whereas a further solution comprising 0.5% citric acid, 80 ppm calcium, pH 3.0 resulted in a loss of at least 40 microns of enamel, the addition of 0.5 g/l sodium polyphosphate to the solution resulted in a loss of about 6 microns of enamel demonstrating a most substantial reduction in erosive effect in the presence of a small quantity of calcium. Use of 0.25 g/l sodium polyphosphate was also effective. Use of 1 g/l sodium polyphosphate was also effective. Use of 3 g/l sodium polyphosphate was less effective. Whereas a solution comprising 0.5% citric acid, pH 3.0 resulted in a loss of at least 40 microns of enamel and the addition of 0.05% xanthan gum to the acid solution resulted in the loss of 5.6 microns of enamel, the addition of 0.5 g/l sodium polyphosphate and 0.05% xanthan gum to the acid solution resulted in a loss of only about 1.2 microns of enamel demonstrating a highly substantial reduction in erosive effect even in the absence of calcium.

The polyphosphate polymer chain length surprisingly is an important aspect of the invention. Solutions were prepared containing approximately equivalent molar concentrations of phosphate groups. Whereas a solution comprising 0.5% citric acid, 80 ppm calcium, pH 3.0 resulted in a loss of at least 40 microns of enamel, the addition of 0.65 g/l sodium phosphate (n=1) to the solution resulted in a loss of about 33 microns of enamel. When the phosphate source used was sodium pyrophosphate (n=2) the loss was estimated to be about 29 microns of enamel and when sodium tri-phosphate (n=3) was employed the loss was about 20 microns of enamel. This contrasts with a loss of only about 6 microns of enamel when 0.5 g/l sodium polyphosphate (n=17) was used.

EXAMPLE 2

The Influence of Polyphosphate Polymer Chain Length

A. Solutions were prepared containing approximately equivalent molar concentrations of phosphate groups dissolved in 0.3% w/v citric acid monohydrate (CAMH), pH 3.4. pH was adjusted by the addition of NaOH as required. Materials were sourced as detailed in Example 1. Additionally sodium polyphosphate n≈4, 7, 28 was from Chemische Fabrik Budenheim, Budenheim, Germany, and sodium polyphosphate n≈12, 21, 25 was from Rhodia Ltd. Widnes, Cheshire, UK. Enamel specimens were placed in the solutions with stirring at 37 C for 4 hours and the amount of enamel lost from the surface during that time measured by profilometry as described previously.

| Phosphate salt | Salt n | Phosphate salt (g/L) | 4 Hr Enamel Loss (microns) |
|---|---|---|---|
| — | 0 | — | 41.9 |
| Sodium phosphate | 1 | 0.65 | 34.05 |
| Tetra sodium pyrophosphate | 2 | 1.08 | 34.9 |
| Penta sodium triphosphate | 3 | 0.61 | 29.6 |
| Sodium polyphosphate | 4 | 0.575 | 23.98 |
| Sodium polyphosphate | 7 | 0.54 | 12.8 |
| Sodium polyphosphate | 12 | 0.49 | 10.02 |
| Sodium polyphosphate | 17 | 0.5 | 8.98 |
| Sodium polyphosphate | 21 | 0.5 | 6.18 |
| Sodium polyphosphate | 25 | 0.5 | 7.2 |
| Sodium polyphosphate | 28 | 0.5 | 10.13 |

Whereas a solution comprising 0.3% citric acid, pH 3.4 resulted in a loss of about 42 microns of enamel, the addition of about 0.5 g/l sodium polyphosphate to the solution resulted in a significant reduction in loss of enamel when the polyphosphate average chain length was 7 or greater.

B. The investigation was conducted in the presence of 80 ppm calcium and the following data obtained. Calcium was added as calcium carbonate.

| Phosphate salt | Salt n | Phosphate salt (g/L) | 4 Hr Enamel Loss (microns) |
|---|---|---|---|
| — | — | — | 42.8 |
| Sodium polyphosphate | 4 | 0.575 | 8.2 |
| Sodium polyphosphate | 7 | 0.54 | 8.59 |
| Sodium polyphosphate | 28 | 0.5 | 2.87 |

Whereas a solution comprising 0.3% citric acid monohydrate, pH 3.4 and 80 ppm calcium resulted in a loss of about 43 microns of enamel, the addition of about 0.5 g/l sodium polyphosphate to tie solution resulted in a significant reduction in loss of enamel when the polyphosphate average chain length was 4 or greater.

C. The investigation was repeated with the conditions altered to 0.5% w/v CAMH, pH3.0 with 80 ppm calcium plus the specified phosphate compound. Sodium polyphosphate with n≈12 was additionally sourced from Albright and Wilson UK Ltd, Oldbury, UK and sodium polyphosphate with n≈20 from Rhodia Ltd.

| Phosphate salt | Salt n | Phosphate salt (g/L) | 4 Hr Enamel Loss (microns) |
|---|---|---|---|
| — | 0 | — | 41.12 |
| Sodium phosphate | 1 | 0.65 | 33.39 |
| Tetra sodium pyrophosphate | 2 | 1.08 | 28.63 |
| Penta sodium triphosphate | 3 | 0.61 | 20.09 |
| Sodium polyphosphate | 4 | 0.575 | 33.20 |
| Sodium polyphosphate | 7 | 0.54 | 25.88 |
| Sodium polyphosphate | 12 | 0.49 | 9.01 |
| Sodium polyphosphate | 12 | 0.49 | 9.63 |
| Sodium polyphosphate | 20 | 0.5 | 9.42 |
| Sodium polyphosphate | 21 | 0.5 | 8.63 |
| Sodium polyphosphate | 25 | 0.5 | 9.13 |
| Sodium polyphosphate | 28 | 0.5 | 14.14 |

Whereas a solution comprising 0.5% citric acid, pH 3.0 and 80 ppm calcium resulted in a loss of about 41 microns of enamel during a 4 hour incubation, the addition of about 0.5 g/l sodium polyphosphate to the solution resulted in a substantial reduction in loss of enamel when the polyphosphate average chain length was greater than 7.

EXAMPLE 3

The Effect of the Concentration of Polyphosphate Polymer

The concentration of polyphosphate applied in the use of the invention is an especially important aspect. In the following demonstrations a sodium polyphosphate with average chain length of 25 phosphate units (Calgon 696, Rhodia Ltd) was used. The acidulant employed was 0.3% w/v citric acid monohydrate. Citric acid is one of the most commonly employed food acidulants. Adjustment of pH where required was achieved by the addition of NaOH. Using the method of Example 1, human dental enamel specimens were exposed to acidic solutions at the given pH in the presence of varying amounts of sodium polyphosphate.

A. At pH2.8

| Sodium polyphosphate g/l | 4 Hr Enamel Loss (microns) |
|---|---|
| 0 | >80 |
| 0.01 | 32.86 |

-continued

| Sodium polyphosphate g/l | 4 Hr Enamel Loss (microns) |
|---|---|
| 0.05 | 19.96 |
| 0.1 | 16.34 |
| 0.4 | 24.86 |
| 0.6 | 30.48 |
| 1 | 19.04 |
| 3 | 48.15 |

Under these highly aggressive conditions where the absence of polyphosphate resulted in an excessive loss of enamel the inclusion of polyphosphate substantially reduced the loss of enamel. In general terms, increasing the quantity of polyphosphate lead to reductions in the loss of enamel. However the inclusion of larger quantities of polyphosphate reversed the trend and resulted in an increase in loss of enamel.

B. At pH3.4

| Sodium polyphosphate g/l | 4 Hr Enamel Loss (microns) |
|---|---|
| 0 | 41.9 |
| 0.01 | 13.21 |
| 0.03 | 8.11 |
| 0.05 | 1.91 |
| 0.075 | 4.92 |
| 0.1 | 4.87 |
| 0.2 | 2.19 |
| 0.4 | 5.2 |
| 0.5 | 12.65 |
| 0.6 | 6.36 |
| 0.8 | 9.65 |
| 1 | 8.02 |
| 1.5 | 12.2 |
| 2 | 25.58 |
| 3 | 43.48 |

Under these conditions where the absence of polyphosphate resulted in a substantial loss of enamel the inclusion of polyphosphate reduced the loss of enamel. In general terms, increasing the quantity of polyphosphate was beneficial and lead to reductions in the loss of enamel. Again the inclusion of larger quantities of polyphosphate reversed the trend and resulted in an increase in loss of enamel.

C. At pH13.8

| Sodium polyphosphate g/l | 4 Hr Enamel Loss (microns) |
|---|---|
| 0 | 23.86 |
| 0.005 | 17.95 |
| 0.01 | 15.13 |
| 0.05 | 2.49 |
| 0.1 | 1.19 |
| 0.4 | 3 |
| 1 | 9.45 |
| 3 | 24.06 |

Under these conditions where the absence of polyphosphate resulted in a substantial loss of enamel the inclusion of polyphosphate reduced the loss of enamel. In general terms, increasing the quantity of polyphosphate was beneficial and lead to reductions in the loss of enamel to very low levels. Again the inclusion of larger quantities of polyphosphate reversed the trend and resulted in an increase in loss of enamel.

EXAMPLE 4

Observations on the pH and Acid Concentration

The invention was advantageously applied to a wide range of pH values and acid concentrations. Solutions were made at the given strength of citric acid monohydrate and sodium polyphosphate with average polymer chain length of 25 (Rhodia Ltd) and adjusted to the named pH with NaOH as required. The solutions were then evaluated for their erosive properties as described in Example 1.

| pH | Citric acid CAMH % w/v | Sodium polyphosphate g/l | 4 Hr Enamel Loss (microns) |
|---|---|---|---|
| 2.9 | 0.6 | 0 | >80 |
| 2.9 | 0.6 | 0.1 | 18.9 |
| 3.2 | 0.3 | 0 | 31.7 |
| 3.2 | 0.3 | 0.1 | 6.4 |
| 3.8 | 0.8 | 0 | 32.0 |
| 3.8 | 0.8 | 0.1 | 8.1 |
| 4.5 | 0.3 | 0 | 9.95 |
| 4.5 | 0.3 | 0.1 | 1.67 |
| 5.5 | 0.3 | 0 | 6.4 |
| 5.5 | 0.3 | 0.1 | 3.5 |

In all cases the inclusion of sodium polyphosphate produced a significant decrease in the erosivity of the acidic solution. Observations are further extended in Example 6.

EXAMPLE 5

The Applicability of the Invention to other Acidulant Species

The invention was advantageously applied to reducing the erosivity of acidulants other than citric acid. Solutions were made at the given strength of D,L malic acid (Aldrich Chemical Co Ltd) or L-lactic acid (BDH Merck Ltd) including sodium polyphosphate with average polymer chain length of 25 (Rhodia Ltd) and adjusted to the named pH with NaOH as required. The solutions were then evaluated for their erosive properties as described in Example 1.

| pH | Acid % w/v | Sodium polyphosphate g/l | 4 Hr Enamel Loss (microns) |
|---|---|---|---|
| 3.5 | 0.4 malic | 0 | 53.5 |
| 3.5 | 0.4 malic | 0.1 | 6.82 |
| 3.2 | 0.3 lactic | 0 | 53.9 |
| 3.2 | 0.3 lactic | 0.1 | 11.6 |

The inclusion of sodium polyphosphate resulted in a significant decrease in the erosivity of the acidic solutions. The applicability to phosphoric acid is described in a further example illustrating reduction in erosivity of cola formulations.

EXAMPLE 6

The Effect of the Combination of Polyphosphate and Viscosity Modulating Polymer on Enamel Erosion The co-administration of sodium polyphosphate with a viscosity modifying polymer such as a food gum resulted in an enhanced reduction in enamel erosion as illustrated by the results of the following experiments. Solutions were made at the given strength of citric acid monohydrate, food hydrocolloid and sodium polyphosphate with average polymer chain length of 25 (Rhodia Ltd). The solutions were adjusted to the named pH with NaOH as required. The solutions were then evaluated for their erosive properties as described in Example 1. Suppliers of food hydrocolloids were Monsanto/Kelco Biopolymers (xanthan gum, "Keltrol RD"), Hercules (carboxymethylcellulose, "Blanose"), ISP Alginates UK Ltd. Tadworth, Surrey (propylene glycol alginate, "Manucol ester M"), Hercules (low and high methoxypectin, "Genu" pectins).

| pH | Citric acid CAMH % w/v | Sodium polyphosphate g/l | Xanthan gum % w/v | 4 Hr Enamel Loss (microns) |
|---|---|---|---|---|
| 3.0 | 0.3 | 0 | 0 | 43.6 |
| 3.0 | 0.3 | 0.075 | 0.05 | 1.36 |

Whereas a solution of 0.3% citric acid monohydrate eroded a mean value of 43.6 microns of enamel from test enamel specimens the co-administration of polyphosphate and xanthan gum resulted in a loss of only 1.36 microns of enamel.

| pH | Citric acid CAMH % w/v | Sodium polyphosphate g/l | Xanthan gum % w/v | 4 Hr Enamel Loss (microns) |
|---|---|---|---|---|
| 2.4 | 0.6 | 0 | 0 | >80 |
| 2.4 | 0.6 | 0 | 0.05 | 24.3 |
| 2.4 | 0.6 | 0.1 | 0.05 | 11.7 |

Under these especially aggressive conditions of pH and acid concentration, the control condition (acid alone) exceeded the capacity of the profilometer to measure the degree of erosion. The addition of 0.05% w/v xanthan gum reduced erosion considerably but the co-administration of xanthan gum and 0.1 g/l sodium polyphosphate further reduced erosion to significant degree.

The following experiment was performed at pH3.2 with 0.3% w/v citric acid monohydrate. Data is provided both in the presence and the absence of the given concentration of sodium polyphosphate.

| Gum % w/v | Sodium polyphosphate g/l | 4 Hr Enamel Loss (microns) |
|---|---|---|
| None | None | 31.7 |
| Xanthan 0.02 | None | 15 |
| Xanthan 0.02 | 0.1 | 0.71 |
| Xanthan 0.03 | None | 9.5 |
| Xanthan 0.03 | 0.05 | 2.8 |
| Xanthan 0.03 | 0.075 | 1.84 |
| Xanthan 0.03 | 0.1 | 0.13 |
| Xanthan 0.05 | None | 7.9 |
| Xanthan 0.05 | 0.075 | 0.41 |
| Xanthan 0.05 | 0.1 | 0.21 |
| Carboxymethylcellulose 0.15 | None | 11.3 |
| Carboxymethylcellulose 0.15 | 0.075 | 3.0 |
| PG alginate 0.4 | None | 6.2 |
| PG alginate 0.4 | 0.1 | 1.4 |
| Low methoxypectin 0.5 | None | 4.3 |
| Low methoxypectin 0.5 | 0.1 | 0.55 |
| High methoxypectin 0.8 | None | 11 |
| High methoxypectin 0.8 | 0.1 | 0.54 |

In all instances the co-administration of food hydrocolloid with sodium polyphosphate resulted in an enhanced reduction in the degree of erosion of dental enamel over that observed with gum alone.

EXAMPLE 7

The Effect of the Combination of Polyphosphate and Calcium on Enamel Erosion

The co-administration of sodium polyphosphate with calcium resulted in an enhanced reduction in enamel erosion as illustrated by the results of the following experiments. The molar ratio of calcium to citric acid employed was 0.14 (with 80 ppm calcium), 0.175 (with 100 ppm calcium) and 0.35 (with 200 ppm calcium). Solutions were made with 0.3% w/v citric acid monohydrate, calcium (BDH Merck) added as calcium carbonate and sodium polyphosphate with average polymer chain length of 25 (Rhodia Ltd). The solutions were adjusted to the named pH with NaOH or sulphuric acid as required. The solutions were then evaluated for their erosive properties as described in Example 1.

| pH | Ca (ppm) | Sodium polyphosphate g/l | 4 Hr Enamel Loss (microns) |
|---|---|---|---|
| 3.2 | 100 | None | 31.5 |
| 3.2 | 100 | 0.075 | 4.5 |
| 3.2 | 100 | 0.1 | 4.4 |
| 3.2 | 200 | None | 25.2 |
| 3.2 | 200 | 0.075 | 3.1 |
| 3.4 | None | None | 41.9 |
| 3.4 | 80 | None | 42.8 |
| 3.4 | None | 0.2 | 11 |
| 3.4 | 80 | 0.2 | 3.5 |

Similarly further experiments evaluated the influence of calcium when the average chain length of sodium polyphosphate employed was 4, 7 and 28, at pH 3.4 with 0.3% w/v citric acid monohydrate. Suppliers of sodium polyphosphate were as given in Example 2.

| Ca (ppm) | Sodium polyphosphate g/l | Polyphosphate av. Chain length | 4 Hr Enamel Loss (microns) |
|---|---|---|---|
| None | 0.575 | 4 | 24.0 |
| 80 | 0.575 | 4 | 8.2 |
| None | 0.54 | 7 | 20.7 |
| 80 | 0.54 | 7 | 8.6 |
| None | 0.5 | 28 | 10.1 |
| 80 | 0.5 | 28 | 2.9 |

A beverage concentrate was prepared using the following ingredients:

| Ingredient | Grams / litre |
|---|---|
| Water | To 1 litre |
| Citric acid monohydrate | 11.25 |
| Trisodium citrate dihydrate | 5.25 |
| Potassium sorbate | 0.8 |
| Flavourings | 5 |
| Aspartame | 1.7 |
| Acesulfame-K | 0.6 |

| Ingredient | Grams / litre |
|---|---|
| Sodium polyphosphate (n ≈ 25) | 1.0 |
| Calcium carbonate | 1.0 |

The concentrate is intended for dilution with 4 parts of water prior to consumption. The concentrate had a pH of approximately 3.75 and contained 400 ppm calcium. The concentrate had a very slight turbidity that could be readily masked by colouring and clouding agents known in the art.

EXAMPLE 8

The Effect of the Combination of Polyphosphate, Viscosity Modulating Polymer and Calcium on Enamel Erosion The co-administration of sodium polyphosphate with a viscosity modifying polymer such as a food gum and calcium resulted in an enhanced reduction in enamel erosion as illustrated by the results of the following experiments. Solutions were made with 0.3% w/v citric acid monohydrate, xanthan-gum (Kelco), calcium (added as calcium carbonate) and sodium polyphosphate with average polymer chain length of 25 (Rhodia Ltd). The solutions were adjusted to the named pH with NaOH or sulphuric acid as required. The solutions were then evaluated for their erosive properties as described in Example 1. The molar ratios of calcium to acid employed ranged from 0.14 to 0.35.

| pH | Xanthan gum % w/v | Sodium polyphosphate g/l | Ca (ppm) | 4 Hr Enamel Loss (microns) |
|---|---|---|---|---|
| 3.2 | 0.05 | 0.075 | 100 | 0.27 |
| 3.2 | 0.05 | 0.1 | 100 | 0.55 |
| 3.2 | 0.02 | 0.1 | 200 | 0.81 |

As can be noted the co-administration of polyphosphate, food gum and calcium resulted in exceptionally low levels of erosion in the assay.

EXAMPLE 9

Application to Fruit Juice Flavoured Beverages

The following fruit drink concentrates for dilution were prepared using the following ingredients. Sodium polyphosphate was added as the final ingredient where applied. In each case the beverage concentrate was adjusted to a pH of 3.2.

Control Drink

| Ingredient | % w/w |
|---|---|
| Water | 64.297 |
| Blackcurrant Juice | 35.0 |
| Ascorbic Acid | 0.271 |
| Aspartame | 0.173 |
| Acesulfame K | 0.058 |
| Potassium Sorbate | 0.079 |
| Flavourings | 0.122 |

Drink with polyphosphate

| Ingredient | % w/w |
|---|---|
| Water | 64.199 |
| Blackcurrant Juice | 35.0 |
| Ascorbic Acid | 0.271 |
| Aspartame | 0.173 |
| Acesulfame K | 0.058 |
| Potassium Sorbate | 0.079 |
| Flavourings | 0.122 |
| Sodium Polyphosphate | 0.0098 |

Drink with polyphosphate and food gum

| Ingredient | % w/w |
|---|---|
| Water | 64.199 |
| Blackcurrant Juice | 35.0 |
| Ascorbic Acid | 0.271 |
| Aspartame | 0.173 |
| Acesulfame K | 0.058 |
| Potassium Sorbate | 0.079 |
| Flavourings | 0.122 |
| Xanthan Gum | 0.147 |
| Sodium Polyphosphate | 0.0098 |

The following table summarises the analtyical characteristics of the fruit drinks.

| Variant | Sodium Polyphosphate (g/L) as RTD* | Xanthan Gum (g/L) as RTD | Acidity (% w/w CAMH) as concentrate | pH as RTD |
|---|---|---|---|---|
| Control | 0 | 0 | 1.22 | 3.27 |
| With sodium polyphosphate | 0.1 | 0 | 1.20 | 3.26 |
| With sodium polyphosphate and xanthan gum | 0.1 | 0.3 | 1.20 | 3.28 |

*RTD is defined as ready to drink i.e. after dilution.

The erosivity of the beverages was evaluated using the method described in Example 1 after dilution of one part with four equal parts of a mineral water (Volvic, Danone Group Ltd). Whereas the control drink without the addition of xanthan gum removed 41 microns of enamel in 4 hours, the beverage including sodium polyphosphate (n≈25, Rhodia Ltd) removed 7 microns but the beverage with the same quantity of polyphosphate and the addition of xanthan gum only removed 1 micron of enamel demonstrating the utility of the invention. All beverages had excellent organoleptic characteristics.

EXAMPLE 10

Application to Sports Drinks

An experimental sport drink formulation was made as per the following list of ingredients with and without the addition of sodium polyphosphate (n=25, Rhodia Ltd).

Isotonic Grapefruit Flavoured Sport Drink

| Ingredient | % w/w |
|---|---|
| Water | 90.31 |
| Carbohydrate Syrup 027* | 8.838 |
| Trisodium citrate dihydrate | 0.195 |

-continued

| Ingredient | % w/w |
|---|---|
| Citric Acid | 0.536 |
| Aspartame | 0.009 |
| Acesulfame K | 0.005 |
| Potassium Sorbate | 0.029 |
| Sodium Benzoate | 0.007 |
| Grapefruit Flavouring | 0.073 |

Isotonic Grapefruit Flavoured Sport Drink (with polyphosphate)

| Ingredient | % w/w |
|---|---|
| Water | 90.29 |
| Carbohydrate Syrup 027* | 8.838 |
| Trisodium citrate dihydrate | 0.195 |
| Citric Acid | 0.536 |
| Aspartame | 0.009 |
| Acesulfame K | 0.005 |
| Potassium Sorbate | 0.029 |
| Sodium Benzoate | 0.007 |
| Grapefruit Flavouring | 0.073 |
| Sodium polyphosphate | 0.0195 |

*Contains glucose syrup and maltodextrin.

Sodium polyphosphate was added as the final ingredient. Analytical characteristics:

| Variant | Sodium polyphosphate (g/L) | Acidity (% w/w CAMH) | pH |
|---|---|---|---|
| Without sodium polyphosphate | 0 | 0.6 | 3.4 |
| With sodium polyphosphate | 0.2 | 0.58 | 3.42 |

Whereas the control formulation without sodium polyphosphate resulted in the loss of 60 microns of enamel after a 4 hour incubation with enamel at 37 C, the test formulation removed only 2.6 microns of enamel, demonstrating the utility of the invention.

EXAMPLE 11

Application to Dry Powdered Drinks

A powdered sport drink formulation was made according to the following list of ingredients that are dry blended typically using a ribbon blender until an homogeneous mixture is obtained. The product is then filled into appropriate packaging such as sachets, jars or drums.

| Ingredients | Kg |
|---|---|
| Dextrose monohydrate | 390 |
| Maltodextrin | 532 |
| Aspartame | 0.58 |
| Acesulfame-k | 0.37 |
| Trisodium citrate | 16.5 |
| Sodium chloride | 9.3 |

-continued

| Ingredients | Kg |
|---|---|
| Citric acid | 37 |
| Ascorbic acid | 1.15 |
| Potassium citrate | 2.3 |
| Orange flavour | 3 |
| Beta carotene (1%) | 5.8 |
| Sodium polyphosphate (n ≈ 25, Rhodia Ltd) | 2 |
| Total | 1000 |

100 g of the powder was dissolved in water to a final volume of 1 litre to make an orange sport drink. The drink had a pH of approximately 4.

EXAMPLE 12

Application to Fruit Juice

Orange juice has been evaluated for its erosive properties in situ. See for example West et al "A method to measure clinical erosion: the effect of orange juice consumption on erosion of enamel." Journal of Dentistry (1998) Vol 26 pp 329-335 and Hughes et al. "Development and evaluation of a low erosive blackcurrant juice drink in vitro and in situ 1. Comparison with orange juice." Journal of Dentistry (1999) Vol 27 pp 285-289 and was found to be moderately erosive. The erosivity of a commercial orange juice (Gerber Soft Drinks, Somerset, UK) was reduced by the addition of 0.1 gl sodium polyphosphate (n≈25, Rhodia Ltd.). This example of pure orange juice (diluted from orange juice concentrate) was characterised and contained 120 mg/l calcium, had a pH of 3.8 and titratable acidity value of 0.7% w/w CAMH. A sample without the addition of sodium polyphosphate removed 21.3 microns of enamel whereas with the addition of sodium polyphosphate 1.6 microns only was removed.

EXAMPLE 13

Application to Cola Beverages

Cola beverages based on phosphoric acid also fall within the scope of the invention. A standard cola and a diet cola, made from commercial materials supplied by Quest Ltd, were manufactured using the following ingredients, both with and without the addition of 0.2 g/l sodium polyphosphate (n≈25, Rhodia Ltd.). The pH of the beverages was approximately 2.8 (standard cola) and 3.4 (diet cola). These were assessed for erosivity as per the previously described method.

Full Sugar Cola

| Ingredient | % w/w |
|---|---|
| Water | 86.98 |
| Sucrose | 12.74 |
| Colour (caramel) | 0.145 |
| Phosphoric Acid | 0.085 |
| Potassium sorbate | 0.038 |
| Caffeine | 0.007 |
| Flavouring | 0.002 |

Full Sugar Cola (with polyphosphate)

| Ingredient | % w/w |
|---|---|
| Water | 86.96 |
| Sucrose | 12.74 |
| Colour (caramel) | 0.145 |
| Phosphoric Acid | 0.085 |
| Potassium sorbate | 0.038 |
| Sodium polyphosphate | 0.019 |
| Caffeine | 0.007 |
| Flavouring | 0.002 |

Diet Cola

| Ingredient | % w/w |
|---|---|
| Water | 99.67 |
| Colour (caramel) | 0.145 |
| Phosphoric Acid | 0.085 |
| Citric acid | 0.018 |
| Aspartame | 0.05 |
| Potassium sorbate | 0.038 |
| Trisodium citrate dihydrate | 0.019 |
| Caffeine | 0.007 |
| Acesulfame K | 0.004 |
| Flavouring | 0.002 |

Diet Cola (with polyphosphate)

| Ingredient | % w/w |
|---|---|
| Water | 99.65 |
| Colour (caramel) | 0.145 |
| Phosphoric Acid | 0.085 |
| Citric acid | 0.018 |
| Aspartame | 0.05 |
| Potassium sorbate | 0.038 |
| Trisodium citrate dihydrate | 0.019 |
| Sodium polyphosphate | 0.019 |
| Caffeine | 0.007 |
| Acesulfame K | 0.004 |
| Flavouring | 0.002 |

The test and control products had the following analytical characteristics:

| Variant | Sodium polyphosphate (g/L) | Acidity (% w/w expressed in terms of CAMH) | pH |
|---|---|---|---|
| Full sugar cola control | 0 | 0.095 | 2.8 |
| Full sugar cola with polyphosphate | 0.2 | 0.098 | 2.84 |
| Diet cola control | 0 | 0.086 | 3.45 |
| Diet cola control with polyphosphate | 0.2 | 0.086 | 3.41 |

Whereas the control full sugar cola removed 42.9 microns of enamel in 4 hours the formulation supplemented with sodium polyphosphate removed only 10.5 microns. Similarly, the control diet cola removed 27.6 microns of enamel in 4 hours. However the formulation supplemented with sodium polyphosphate removed only 6 microns. Both these examples demonstrate the substantial reduction in erosive power that may be made using the invention.

EXAMPLE 14

Application to Flavoured Acidified Waters

Those skilled in the art of beverage manufacture will appreciate that the invention may be applied to diverse beverages, both unsweetened and sweetened, either of low or conventional calorific content made with artificial sweeteners or carbohydrate sweeteners. By way of example a lemonade was made according to the following schedule of ingredients.

| Ingredient | Grams per litre syrup |
|---|---|
| Citric acid monohydrate | 11.25 |
| Trisodium citrate dihydrate | 5.25 |
| Sodium benzoate | 0.5 |
| Aspartame | 1.15 |
| Acesulfame-k | 1.8 |
| Flavouring - lemon | 5 |
| Sodium polyphosphate (n ≈ 25, Rhodia Ltd.) | 1 |
| Water | To 1 litre |

Finished product was made by mixing one part syrup with four parts carbonated water and had a pH of approximately 3.4. Optionally the syrup can contain food hydrocolloids, for example 1 gram per litre xanthan gum.

EXAMPLE 15

Application to Confectionery and Diverse Acidic Lozenges

Acidic confectionery may be erosive; for example see. Lussi et al, "Erosion on abraded dental hard tissues by acid lozenges: an in situ study" Clin Oral Invest (1997) 1: 191-194. Solid formats such as acidic confectionery may be made less erosive by the application of the invention. A pastille was made according to the following schedule.

| Ingredient | Grams / batch |
|---|---|
| Sucrose | 180 |
| Glucose syrup 42DE | 120 |
| Water | 90 |

Boil above mix until a value of 80 degrees brix is achieved, remove 260 g, cool to 100 degrees C. and add to dissolved gelatin mix detailed below. Mix thoroughly.

| Ingredient | Grams/batch |
|---|---|
| Boiling water | 93.5 |
| Gelatin - 150 bloom | 32 |
| Blackcurrant juice 5 fold concentrate | 8 |
| Citric acid | 0.8 |
| Flavouring | 4 |
| Sodium polyphosphate (n ≈ 25, Rhodia Ltd) | 0.25 |
| Aspartame | 0.12 |
| Acesulfame-k | 0.06 |

Deposit into starch moulds. Place filled moulds into biscuit oven at 50 C for 2 hours. Remove pastilles from moulds when cool. Similar examples may readily be made by substitution of the sugars sucrose/glucose from a selection of sugars of reduced cariogenic potential such as sugar alcohols, trehalose and diverse sweetening/bulking agents known in the art.

EXAMPLE 16

Application to Frozen Acidic Comestibles

A solution was prepared by mixing ingredients as follows:

| Ingredient | % w/w |
|---|---|
| Sugar | 20 |
| Orange juice | 5 |
| Ascorbic acid | 0.03 |
| Citric acid monohydrate | 0.225 |
| Trisodium citrate dihydrate | 0.11 |
| Flavouring | 0.1 |
| Sodium polyphosphate (n ≈ 25) | 0.02 |
| Water | To 100 |

The solution had a pH of approximately 3.4. The solution can-be solidified by freezing, preferably at temperatures around minus 20 degrees C.

The invention claimed is:

1. A process for preparing an acidic orally administrable composition comprising
1) providing a first acidic orally administrable composition;
2) adding to said first orally administrable composition:
   a) a polyphosphate polymer having at least three phosphate groups and wherein the polyphosphate polymer concentration is in the range 0.005 to 3.0 g/l;
   b) a viscosity modifying polymer selected from hydrocolloids, alginates, locust bean gum, gellan gum, guar gum, gum arabic, tragacanth, carrageenan, acacia gum, xanthan gums, pectins, celluloses, polyvinylpyrrolidone (PVP), and combinations or mixtures thereof; and
   c) a calcium salt present in an amount from 0.1 to 0.8 mols of calcium per mol of acid; and
   d) adjusting the effective pH of the composition to 2.2 to 5.5 and wherein the composition has a titratable acidity from 0.01 to 0.4% w/w; and
3) thereby providing a second acidic orally administrable composition which has a lower tooth erosion potential than said first acidic orally administrable composition.

2. A method of reducing tooth erosion in a mammal comprising
1) providing a first acidic orally administrable composition;
2) adding to said first acidic orally administrable composition
   a) a polyphosphate polymer having at least three phosphate groups; and
   b) a viscosity modifying polymer selected from hydrocolloids, alginates, locust bean gum, gellan gum, guar gum, gum arabic, tragacanth, carrageenan, acacia gum, xanthan gums, pectins, celluloses, polyvinylpyrrolidone (PVP), and combinations or mixtures thereof; and
   c) and a calcium salt present in an amount from 0.1 to 0.8 mols of calcium per mol of acid;
3) thereby providing a second acidic orally administrable composition; wherein the amounts of a), b) and c) added in step 2) are controlled to provide an effective pH from 2.2 to 5.5, and a titratable acidity from 0.01 to 0.4% w/w; and the polyphosphate polymer concentration in the second acidic composition is in the range of 0.005 to 3.0 g/l; in which the second acidic orally administrable composition has a lower tooth erosion potential than said first acidic orally administrable composition; and
4) orally administering said second acidic orally administrable composition to a mammal in need thereof.

3. The method according to claim 2 wherein the second acidic composition is a liquid, solid or semi-solid.

4. A method of reducing tooth erosion in a mammal comprising
1) providing a first acidic orally administrable composition;
2) adding to said first acidic orally administrable composition
   a) a polyphosphate polymer having at least three phosphate groups; and
   b) a viscosity modifying polymer comprising an alginate; and
   c) a calcium salt present in an amount from 0.1 to 0.8 mol of calcium salt per mol of acid;
3) thereby providing a second acidic orally administrable composition; wherein the amounts of a), b) and c) added in step 2) are controlled to provide an effective pH at which the second acidic orally administrable composition has a lower tooth erosion potential than said first acidic orally administrable composition and wherein the composition has a titratable acidity from 0.01 to 0.4% w/w; and wherein the polyphosphate polymer concentration in the second acidic composition is in the range 0.005 to 3.0 g/l; and
4) orally administering said second acidic orally administrable composition to a mammal in need thereof.

5. The method according to claim 2 wherein the polyphosphate polymer has is at least 7 phosphate groups.

6. The method according to claim 2 wherein the polyphosphate polymer has at least 12 phosphate groups.

7. The method according to claim 2 wherein the polyphosphate polymer is sodium polyphosphate having an average number of phosphate groups (n) in the range 7 to 30.

8. The method according to claim 2 wherein the concentration of polyphosphate in the second acidic composition, expressed as the concentration of sodium polyphosphate, is in the range 0.01 to 1.5 g/l.

9. The method according to claim 2 wherein the viscosity modifying polymer is an alginate, a xanthan, a cellulose or a pectin.

10. The method according to claim 3 wherein the second acidic composition is a beverage, a liquid or solid concentrate for the preparation of a beverage, or a confectionery product.

11. The method according to claim 10 wherein the beverage has a pH in the range of 2.4 to 4.5.

12. The method according to claim 10 wherein the beverage has a titratable acidity in the range 0.1 to 2.5% w/w.

13. The method according to claim 4 wherein the polyphosphate polymer has at least 7 phosphate groups.

14. The method according to claim 13 wherein the polyphosphate polymer has at least 12 phosphate groups.

15. The method according to claim 4 wherein the polyphosphate polymer is sodium polyphosphate having an average number of phosphate groups in the range 7 to 30.

16. The method according to claim 4 wherein the polyphosphate polymer concentration in the second acidic composition, expressed as the concentration of sodium polyphosphate, is in the range 0.01 to 1.5 g/l.

17. The method according to claim 4 wherein the effective pH of the second acidic composition is in the range 2.2 to 5.5.

18. The method according to claim 4 wherein the second acidic composition is a liquid, solid or semi-solid.

19. The method according to claim 18 wherein the second acidic composition is a beverage, a liquid, or solid concentrate for the preparation of a beverage, or a confectionery product.

20. The method according to claim 19 wherein the second acidic composition is a beverage and has a titratable acidity in the range 0.1 to 2.5% w/w.

21. The method according to claim 2 wherein the polyphosphate polymer has is from 12 to 28 phosphate groups.

22. The method according to claim 10 wherein the beverage has a pH in the range of pH range 2.7 to 4.0.

23. The method according to claim 2 wherein the molar ratio of the calcium to acid is from 0.1 to 0.6.

24. The method according to claim 2 wherein the molar ratio of the calcium to acid is from 0.1 to 0.5.

25. The method according to claim 2 wherein the calcium concentration in the second acidic composition is more than 0.05 mol per litre.

26. The method according to claim 2 wherein the calcium concentration in the second acidic composition is more than 0.01 mol per litre.

27. The method according to claim 1 wherein the molar ratio of the calcium to acid is from 0.1 to 0.6.

28. The method according to claim 1 wherein the molar ratio of the calcium to acid is from 0.1 to 0.5.

29. The method according to claim 2 wherein the calcium concentration in the second acidic composition is more than 0.05 mol per litre.

30. The method according to claim 2 wherein the calcium concentration is more than 0.01 mol per litre.

31. The method according to claim 2 wherein the effective pH of the composition is from 2.4 to 4.5.

32. The process according to claim 1 wherein the viscosity modifying agent is a methoxy pectin, ester pectin, amidated pectin, alginate, sodium alginate, propylene glycol alginate, or mixture thereof.

33. The method according to claim 2 wherein the viscosity modifying agent is agent is a methoxy pectin, ester pectin, amidated pectin, alginate, sodium alginate, propylene glycol alginate, or mixture thereof.

34. The method according to claim 4 wherein the viscosity modifying agent is a methoxy pectin, ester pectin, amidated pectin, alginate, sodium alginate, propylene glycol alginate, or mixture thereof.

* * * * *